United States Patent
Li et al.

(10) Patent No.: US 9,050,277 B2
(45) Date of Patent: Jun. 9, 2015

(54) **COMBINED *GEUM JAPONICUM* AND *CENTELLA ASIATICA* EXTRACTS FOR THE THERAPEUTIC TREATMENT OF HEART FAILURE**

(75) Inventors: Ming Li, Hong Kong (HK); Zhongyu Li, Heilongjiang (CN)

(73) Assignee: Generex Pharmaceuticals, Inc., Grand Kayman (KY)

( * ) Notice: Subject to any disclaimer, the term of this patent is extended or adjusted under 35 U.S.C. 154(b) by 0 days.

(21) Appl. No.: 13/377,483

(22) PCT Filed: Jun. 11, 2010

(86) PCT No.: PCT/IB2010/001410
§ 371 (c)(1),
(2), (4) Date: Dec. 9, 2011

(87) PCT Pub. No.: WO2010/143058
PCT Pub. Date: Dec. 16, 2010

(65) Prior Publication Data
US 2012/0077762 A1    Mar. 29, 2012

Related U.S. Application Data

(60) Provisional application No. 61/186,709, filed on Jun. 12, 2009, provisional application No. 61/187,905, filed on Jun. 17, 2009.

(51) Int. Cl.
| | | |
|---|---|---|
| *A61K 36/00* | (2006.01) | |
| *A61K 36/23* | (2006.01) | |
| *A61K 36/73* | (2006.01) | |
| *A61K 31/56* | (2006.01) | |
| *A61K 31/565* | (2006.01) | |
| *A61K 31/7028* | (2006.01) | |
| *A61K 31/7032* | (2006.01) | |
| *A61K 31/7034* | (2006.01) | |

(52) U.S. Cl.
CPC .......... *A61K 36/00* (2013.01); *A61K 31/56* (2013.01); *A61K 31/565* (2013.01); *A61K 31/7028* (2013.01); *A61K 31/7032* (2013.01); *A61K 31/7034* (2013.01); *A61K 36/23* (2013.01); *A61K 36/73* (2013.01)

(58) Field of Classification Search
None
See application file for complete search history.

(56) References Cited

U.S. PATENT DOCUMENTS

| | | |
|---|---|---|
| 5,595,743 A | 1/1997 | Wu |
| 2002/0068098 A1 | 6/2002 | Babish et al. |
| 2005/0064048 A1 | 3/2005 | Li et al. |
| 2008/0260704 A1 | 10/2008 | Riordan et al. |
| 2009/0022827 A1 | 1/2009 | Li et al. |

FOREIGN PATENT DOCUMENTS

| | | |
|---|---|---|
| CN | 1069629 | 3/1993 |
| CN | 1279970 | 1/2001 |
| CN | 1437973 | 8/2003 |
| CN | 1515311 | 7/2004 |
| CN | 1558769 | 12/2004 |
| CN | 1682788 | 10/2005 |
| CN | 1708313 | 12/2005 |
| CN | 101040901 | 9/2007 |
| CN | 101091751 | 12/2007 |
| CN | 101099770 | 1/2008 |
| CN | 101125171 | 2/2008 |
| CN | 101274012 | 10/2008 |
| CN | 101406537 | 4/2009 |
| JP | 2002-255804 | 9/2002 |
| JP | 2003-342190 | 12/2003 |
| JP | 2005-514360 | 5/2005 |
| JP | 2006-347967 | 12/2006 |
| JP | 2007-204447 | 8/2007 |
| JP | 2008-007417 | 1/2008 |
| JP | 2008-074801 | 4/2008 |
| KR | 100718602 | 5/2007 |
| KR | 2009-0020279 | 2/2009 |
| KR | 20090020279 | 2/2009 |
| WO | WO-02/09720 | 2/2002 |
| WO | WO-02/078685 | 10/2002 |
| WO | WO-03/043645 | 5/2003 |
| WO | WO 03043645 A1 * | 5/2003 ............ A61K 35/78 |
| WO | WO-2004/052381 | 6/2004 |
| WO | WO-2005/034958 | 4/2005 |
| WO | WO-2006/054370 | 5/2006 |
| WO | WO-2007/048352 | 5/2007 |
| WO | WO-2007/048353 | 5/2007 |
| WO | WO-2007/049088 | 5/2007 |

(Continued)

OTHER PUBLICATIONS

Yoshida, Okuda, Mwmon and Shingu. Tannins of Rosaceous Medicinal Plants. Part 2.' Gemins A, B, and C, New Dimeric Ellagitannins from *Geum japonicum*. J. Chem. Soc Perkin Trans I, 1985, pp. 315-321.*

(Continued)

*Primary Examiner* — Shaojia Anna Jiang
*Assistant Examiner* — Dale R Miller
(74) *Attorney, Agent, or Firm* — Foley & Lardner LLP

(57) ABSTRACT

Disclosed herein are compounds, extracts, and active fractions of the plant *Geum japonicum* alone or in combination with *Centella Asiatica* and methods for preventing or treating heart failure. The compounds provided herein can be formulated into pharmaceutical compositions and medicaments that are useful in the disclosed methods. Also provided are the use of the compounds and extracts in preparing pharmaceutical formulations and medicaments.

12 Claims, 4 Drawing Sheets

(56) References Cited

FOREIGN PATENT DOCUMENTS

| WO | WO-2007/049089 | 5/2007 |
|---|---|---|
| WO | WO-2007/106049 | 9/2007 |
| WO | WO-2008/144706 | 11/2008 |
| WO | WO-2010/143058 | 12/2010 |
| WO | WO-2010/143059 | 12/2010 |
| WO | WO-2010/143061 | 12/2010 |
| WO | WO-2010/143062 | 12/2010 |
| WO | WO-2010/143063 | 12/2010 |
| WO | WO-2010/143065 | 12/2010 |

OTHER PUBLICATIONS

Pragada, R. R., Veeravalli, K. K., Chowdary, K. P. R., & Routhu, K. V. (2004). Cardioprotective activity of *Hydrocotyle asiatica* L. in ischemia-reperfusion induced myocardial infarction in rats. Journal of ethnopharmacology, 93(1), 105-108.*
Brinkhaus, B., Lindner, M., Schuppan, D., & Hahn, E. G. (2000). Chemical, pharmacological and clinical profile of the East Asian medical plant *Centella aslatica*. Phytomedicine, 7(5), 427-448.*
Bonfill, M., Mangas, S., Cusidó, R. M., Osuna, L., Pinôl, M. T., & Palazón, J. (2006). Identification of triterpenoid compounds of *Centella asiatica* by thin-layer chromatography and mass spectrometry. Biomedical Chromatography, 20(2), 151-153.*
Adams, K. F., Gheorghiade, M., Uretsky, B. F., Patterson, J. H., Schwartz, T. A., & Young, J. B. (2002). Clinical benefits of low serum digoxin concentrations in heart failure. Journal of the American College of Cardiology, 39(6), 946-953.*
Lapornik, B., Prošek, M., & Golc Wondra, A. (2005). Comparison of extracts prepared from plant by-products using different solvents and extraction time. Journal of Food Engineering, 71(2), 214-222.*
Turkmen, N., Sari, F., & Velioglu, Y. S. (2006). Effects of extraction solvents on concentration and antioxidant activity of black and black mate tea polyphenols determined by ferrous tartrate and Folin-Ciocalteu methods. Food Chemistry, 99(4), 835-841.*
Meredith, P. A., & Östergren, J. (2006). Review: From Hypertension to Heart Failure—Are There Better Primary Prevention Strategies?. Journal of Renin-Angiotensin-Aldosterone System, 7(2), 64-73.*
Lobmeyer, M. T., Gong, Y., Terra, S. G., Beitelshees, A. L., Langaee, T. Y., Pauly, D. F., . . . & Johnson, J. A. (2007). Synergistic polymorphisms of β1 and α2c-adrenergic receptors and the influence on left ventricular ejection fraction response to β-blocker therapy in heart failure. Pharmacogenetics and genomics, 17(4), 277-282.*
Final Office Action issued in U.S. Appl. No. 13/377,489 mailed May 22, 2013 (16 pages).
NDIC, "Diagnosis of Diabetes", Internet Archive Date: Feb. 28, 2005 [Retrieved from internet on: May 18, 2013 by USPTO Examiner]. Retrieved from the Internet: <URL: http://web.archive.org/web/20050228073517/http://diabetes.niddk.nih.gov/dm/pubs/diagnosis/>(7 pages).
Bhattachrya, Salil K. et al., "Effect of Bioactive Tannoid Principles of Emblica Officinalis on Ischemia-Reperfusion-Induced Oxidative Stress in Rat Heart," Phytomedicine, vol. 9, No. 2, Jan. 1, 2002, pp. 171-174.
Fogo, A.S et al., "Tormentic acid reduces vascular smooth muscle cell proliferation and survival," European Journal of Pharmacology, vol. 615, No. 1-3, Aug. 1, 2009, pp. 50-54.
Search Report issued in European Application No. 10785821.9 dated Feb. 15, 2013 (10 pages).
Search Report received in European Application No. 10785818.5 dated Feb. 19, 2013 (11 pages).
EUFICReview, Web publication date: Nov. 1998 [Examiner retrieved from the internet on: Mar. 25, 2013], Retrieved from URL: http://www.eufic.org/article/en/expid/review-diet-lifestyle-life-expectancy/ (6 pages).
Non-Final Office Action issued for U.S. Appl. No. 13/377,501 mailed on Mar. 28, 2013 (17 pages).
Dong, H., et al., "Effects of Tannins from *Geum japonicum* on the Catalytic Activity of Thrombin and Factor Xa of Blood Coagulation Cascade," J. Nat. Prod., Oct. 1998, vol. 61, No. 11, pp. 1356-1360.

International Preliminary Report on Patentability received for PCT/IB2010/001410 mailed Dec. 12, 2011.
International Preliminary Report on Patentability received for PCT/IB2010/001412 mailed Dec. 12, 2011.
International Preliminary Report on Patentability received for PCT/IB2010/001415 mailed Dec. 12, 2011.
International Preliminary Report on Patentability received for PCT/IB2010/001416 mailed Dec. 12, 2011.
International Preliminary Report on Patentability received for PCT/IB2010/001418 mailed Dec. 12, 2011.
International Preliminary Report on Patentability received for PCT/IB2010/001426 mailed Dec. 12, 2011.
International Search Report received for PCT/IB2010/001415 mailed Oct. 21, 2010.
International Search Report received for PCT/IB2010/001410 mailed Nov. 11, 2010.
International Search Report received for PCT/IB2010/001412 mailed Nov. 11, 2010.
International Search Report received for PCT/IB2010/001416 mailed Nov. 11, 2010.
International Search Report received for PCT/IB2010/001418 mailed Nov. 11, 2010.
International Search Report received for PCT/IB2010/001426 mailed Nov. 11, 2010.
Li, J., "Studies on Bioactive Constituents with Myogenesis and Angiogenesis Activity from *Geum japonicum* Thunb" Vax. Chinese F. Bolle, Chinese Doctoral Dissertation & Master's Thesis, Medicine and Health Sciences, Jan. 2007, 41 pages. (English abstract provided).
Liu, H., et al., "Fatty Acid Synthase Inhibitors from *Geum japonicum* Thunb. var. Chinese," Chemistry & Biodiversity, Mar. 24, 2009, vol. 6, Issue 3, pp. 402-410.
Ming, D.S., et al. "Research Progress in Chemical Constituents and Biological Activities of Geum Species," Acta Pharmaceutica Sinica, 2000, vol. 35, No. 7, pp. 552-558.
Yoshiki, K., et al. "Antitumor agents, 129.1 Tannins and Related Compounds as Selective Cytotoxic Agents," Journal of Natural Products, Aug. 1992, vol. 55, No. 8, pp. 1033-1043.
Zeng, F., et al., "The Anticoagulant Effects of *Geum japonicum* Extract and its Constituents," Phytotherapy Research, Mar. 1998, vol. 12, pp. 146-148.
Extended Search Report received in European Application No. 10785823.5 dated Nov. 8, 2012 (12 pages).
Extended Search Report received in European Application No. 10785819.3 dated Nov. 8, 2012 (10 pages).
Extended Search Report received in European Application No. 10785822.7 dated Nov. 8, 2012 (9 pages).
Extended Search Report received in European Application No. 10785820.1 dated Nov. 13, 2012 (7 pages).
International Preliminary Report on Patentability issued for PCT/IB2010/001418 mailed Nov. 22, 2012 (7 pages).
Kang, Soon Ah et al., "Antiinflammatory Activity of the Medicinal Plant *Geum japonicum*," Nutritional Sciences, vol. 9, No. 2, (May 1, 2006), pp. 117-123.
Li, Ming et al., "Repair of Infarcted Myocardium by an Extract of *Geum japonicum* with Dual Effects on Angiogenesis and Myogenesis," Clinical Chemistry, vol. 52, No. 8, (Aug. 1, 2006), pp. 1460-1468.
Myeong-Sim, Ji et al., "Anticoagulant 1,2,3,4,6-pentagalloyl-beta-D-glucopyranos e isolated from geranium (Pelargonium inquinans Ait)," Archives of Pharmacal Research, vol. 28, No. 9, (Sep. 2005), pp. 1037-1041.
Non-Final Office Action received in U.S. Appl. No. 13/377,489 dated Nov. 21, 2012 (9 pages).
Samuels, Noah, "Herbal remedies and anticoagulant therapy," Thrombosis and Haemostasis, vol. 93, No. 1 (Jan. 1, 2005), pp. 3-7.
Somova, L.O. et al., "Cardiovascular, Antihyperlipidemic and Antioxidant Effects of Oleanolic and Ursolic Acids in Experimental Hypertension," Phytomedicine, vol. 10, No. 2-3, (Jan. 1, 2003), pp. 115-121.

(56) References Cited

OTHER PUBLICATIONS

Xie, Yi-Wu et al., "Role of Nitric Oxide in the Vasorelaxant and Hypotensive Effects of Extracts and Purified Tannins from *Geum japonicum*," Journal of Ethnopharmacology, vol. 109, (2007), pp. 128-133.
Final Office Action received in U.S. Appl. No. 13/377,501 mailed Sep. 20, 2013 (12 pages).
Anderson, Koren J. et al., "Walnut Polyphenolics Inhibit in Vitro Human Plasma and LDL Oxication 1,2," Jnl of Nutrition, (2001), 131(11), pp. 2837-2842.
Definitions of "Ischemic Heart Disease" and "Coronary Heart Disease" from Hyperdictionary, retreived on Sep. 11, 2013 from http://hyperdictionary.com.
Fukuda, Toshiyuki et al., "Antioxidative polyphenols from walnuts (*Juglans regia* L.)," Phytochemistry, (2003), 63(7), pp. 795-801.
Larrosa, Mar et al., "Ellagitannins, ellagic acid and vascular health," Molecular Aspects of Medicine, (2010), 31(6), pp. 513-539.
Non-Final Office Action issued in U.S. Appl. No. 13/377,503 mailed Aug. 30, 2013 (28 pages).
Wojtczak, Dr. Andrzej, "Glossary of Medical Education Terms: 'Prevention'," (Feb. 2002), 5 pages.
Yoshida, Takashi et al., "Dimeric ellagitannins, laevigatins E, F and G from *Rosa laevigata*," Phytochemistry, (1989), vol. 28, No. 9, pp. 2451-2454.
Examination Report No. 1 received in Australian Patent Application No. 2010258358 issued Oct. 15, 2014, 5 pages.
Bhattacharya, Salil K. et al., "Effect of bioactive tannoid principles of Emblica officinalis on ischemia-reperfusion-induced oxidative stress in rat heart," Phytomedicine, (2002), vol. 9, pp. 171-174.
Dong-Sheng, Ming et al., "Research Progress in Chemical Constituents and Biological Activities of Geum Species," Acta Pharma, (2000), vol. 35, No. 7, pp. 552-558.
Final Office Action received in U.S. Appl. No. 13/377,503 mailed Apr. 2, 2014 (18 pages).
Office action received in Japanese Patent Application No. 2012-514548 issued Jun. 16, 2014, 7 pages, with English translation.
Office Action received in Japanese Patent Application No. 2012-514549 issued Jul. 2, 2014, 5 pages with English translation.
Office Action received in Japanese Patent Application No. 2012-514550 issued May 21, 2014, 6 pages with English translation.
Office Action received in Japanese Patent Application No. 2012-514551 issued Jun. 30, 2014, 9 pages with English translation.
Office Action received in Japanese Patent Application No. 2012-514552 issued May 28, 2014, 6 pages, with English translation.
Office Action received in Japanese Patent Application No. 2012-514554 issued May 28, 2014, 8 pages, with English Translation.
Patent Examination Report No. 1 received in Australian Patent Application No. 2010258351 issued Jul. 31, 2014, 4 pages.
Patent Examination Report No. 1 received in Australian Patent Application No. 2010258352 issued Jul. 7, 2014, 4 pages.
Patent Examination Report No. 1 received in Australian Patent Application No. 2010258354 issued Jul. 11, 2014, 3 pages.
Patent Examination Report No. 1 received in Australian Patent Application No. 2010258355 issued Jul. 31, 2014, 3 pages.
Ansel, Howard C. et al., Seventh Edition, Pharmaceutical Dosage Forms and Drug Delivery Systems, "Chapter 2: New Drug Development and Approval Process," (1999), 6 pages.
Non-Final Office Action received in U.S. Appl. No. 13/377,501 issued Jan. 2, 2015, 17 pages.
Non-Final Office Action received in U.S. Appl. No. 13/377,503 mailed Jan. 6, 2015, 28 pages.
Non-Final Office Action received in U.S. Appl. No. 13/377,489 mailed Jan. 5, 2015, 21 pages.
Office Action on Japanese Application 2012-514551, mailed Feb. 23, 2015, English translation provided.
Office Action on Japanese Application 2012-514554, mailed Feb. 25, 2015, English translation provided.
Office Action on Japanese Application 2012-514549, mailed Feb. 23, 2015, English translation provided.
Final Rejection on Japanese Application 2012-514550, mailed Feb. 2, 2015 (English translation included).

* cited by examiner

COMBINED *GEUM JAPONICUM* AND *CENTELLA ASIATICA* EXTRACTS FOR THE THERAPEUTIC TREATMENT OF HEART FAILURE

CROSS-REFERENCE TO RELATED APPLICATIONS

The present application is the U.S. National Stage Application of PCT International Application No. PCT/IB2010/001410, filed Jun. 11, 2010, which claims priority to U.S. Provisional Application No. 61/186,709, filed Jun. 12, 2009, and U.S. Provisional Application No. 61/187,905, filed Jun. 17, 2009, the entire contents of which are hereby incorporated by reference in their entirety.

BACKGROUND

The following description is provided to assist the understanding of the reader. None of the information provided or references cited is admitted to be prior art to the present invention.

Heart failure (HF) is the consequence of multiple pathophysiological alterations and adaptations, leading to left ventricular (LV) hypertrophy, dysfunction and dilatation, increased systemic vascular resistance and activation of the neuroendocrine system. Effective treatment for HF has drawn increasingly extensive attention due to the high morbidity and mortality and the severe limitations of currently available therapeutic approaches towards the treatment of HF. HF is a life-threatening condition and one of the major causes of mortality and morbidity in Western countries and becoming so in developed regions of Asia, such as in Hong Kong and China. There are approximately 5 million people living with HF and around 550,000 new cases diagnosed each year in United States alone. Despite the significant improvements in the medical therapy of HF in recent decades, HF remains the leading cause of hospitalization in people older than 65 with an annual mortality of 10% and 50% after 5 years.

HF is characterized by alteration of hemodynamic parameters (preload and cardiac output) with subcellular abnormalities that are associated with stimulus to hypertrophy insufficient to maintain adequate cardiac output. Although extensive research associated with HF has been focused on identification, quantification, and characterization of the injured tissue, evaluation of different therapeutic modalities, and understanding the underlying mechanism of HF, there is no currently effective treatment modality for HF. However, the pace of worsening of HF can be slowed down by treating the underlying conditions.

SUMMARY

The present invention relates to a composition of compounds comprised of triterpenoids and polyphenols for the treatment of heart failure (HF). In one aspect, the present invention provides a method of treating or preventing heart failure in a mammalian subject in need thereof, comprising administering to the mammalian subject an effective amount of a triterpenoid polyphenol composition (TPs), wherein the triterpenoid polyphenol composition comprises:

(i) one or more triterpenoids selected from the group consisting of: Asiatic acid, Niga-ichigoside F1, Kaji-ichigoside F1, Euscaphic acid, Asiaticoside, Tormentic acid, and Madecassic acid, and (ii) one or more polyphenols selected from the group consisting of: Gemin A, Casuarinin, Tellimagrandin II, Potentillin and ellagic acid. In one embodiment, the triterpenoid polyphenol composition comprises Asiatic acid, Niga-ichigoside F1, Kaji-ichigoside F1, Euscaphic acid, Asiaticoside, Tormentic acid, Madecassic acid, Gemin A, Casuarinin, Tellimagrandin II, Potentillin and ellagic acid.

In one embodiment, the heart failure results from hypertension; ischemic heart disease; exposure to a cardiotoxic compound; myocarditis; thyroid disease; viral infection; gingivitis; drug abuse; alcohol abuse; pericarditis; atherosclerosis; vascular disease; hypertrophic cardiomyopathy; acute myocardial infarction; left ventricular systolic dysfunction; coronary bypass surgery; starvation; an eating disorder; or a genetic defect. In one embodiment, the subject is a human.

In one embodiment, the composition is administered orally, topically, systemically, intravenously, subcutaneously, intraperitoneally, or intramuscularly. In one embodiment, the composition is administered in an amount from about 0.01 mg/kg/day to about 2000 mg/kg/day. In one embodiment, the effective amount of the composition is in the form of a formulation comprising the composition and a pharmaceutically acceptable carrier.

In one embodiment, the method further comprises administering an additional therapeutic agent selected from the group consisting of: diuretics, ACE inhibitors, digoxin, and beta-blockers.

In another aspect, the present invention provides a method for preventing or treating heart failure in a mammalian subject, the method comprising: administering to a subject in need thereof an effective amount of an organic extract of *Geum japonicum*.

In one embodiment, the extract is administered in an amount ranging from about 0.001 mg to about 2000 mg of the extract per kilogram of subject body weight per day. In one embodiment, the extract is administered orally. In one embodiment, the extract is administered by subcutaneous injection, intramuscular injection, or intravenous infusion. In one embodiment, the extract is a lower alkyl alcohol extract of *Geum japonicum*. In one embodiment, the lower alkyl alcohol has 1-6 carbons atoms. In one embodiment, the lower alkyl alcohol is ethanol.

In another aspect, the present invention provides a pharmaceutical composition for treating heart failure in a mammalian subject comprising an effective amount of a triterpenoid polyphenol composition, wherein the triterpenoid polyphenol composition comprises:

(i) one or more triterpenoids selected from the group consisting of: Asiatic acid, Niga-ichigoside F1, Kaji-ichigoside F1, Euscaphic acid, Asiaticoside, Tormentic acid, and Madecassic acid, and (ii) one or more polyphenols selected from the group consisting of: Gemin A, Casuarinin, Tellimagrandin II, Potentillin and ellagic acid. In one embodiment, the triterpenoid polyphenol composition comprises Asiatic acid, Niga-ichigoside F1, Kaji-ichigoside F1, Euscaphic acid, Asiaticoside, Tormentic acid, Madecassic acid, Gemin A, Casuarinin, Tellimagrandin II, Potentillin and ellagic acid.

In another aspect, the present invention provides a pharmaceutical composition for treating heart failure in a mammalian subject comprising an effective amount of an organic extract of *Geum japonicum* and a pharmaceutically acceptable carrier. In one embodiment, the organic extract is an ethanol extract. In one embodiment, the organic extract is a methanol extract.

DETAILED DESCRIPTION

Figure 1:
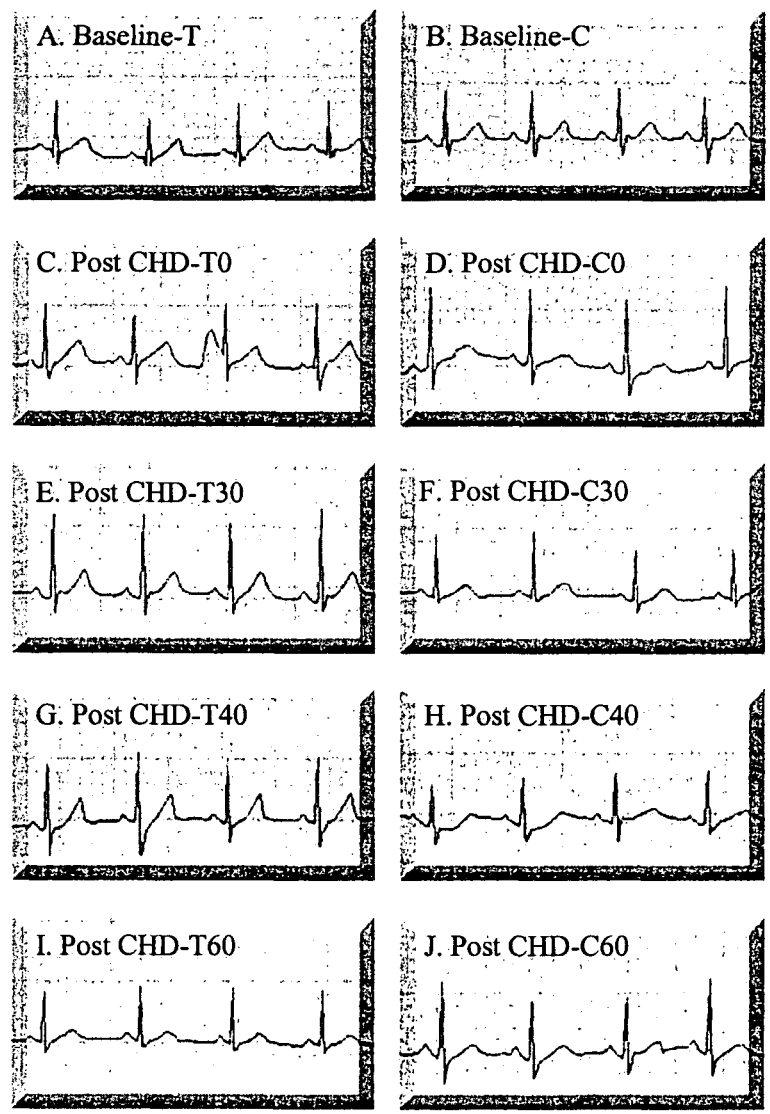
FIG. 1 presents data showing ECG measurement. T denotes TPs treated group, and C denotes the vehicle treated control group. Baseline-T and Baseline-C, The ECG graphs taken before surgery and treatment for both groups. Post CHD-T0 and Post CHD-C0, The ECG graphs taken right on the day of surgery completion for both groups. Post CHD-T30 and Post CHD-C30, Thirty days post CHD surgery before any treatment showing significantly lowered ST segments in both groups. Post CHD-T40 and Post CHD-C40, Forty days after surgery and TPs treatment or vehicle treatment for 10 days. Post CHD-T60 and Post CHD-C60, Sixty days post surgery and APs or vehicle treatment for 30 days.

In various aspects, the present invention provides compounds, extracts, and methods for preventing or treating heart failure. The compounds provided herein can be formulated into pharmaceutical compositions and medicaments that are useful in the disclosed methods. Also provided are the use of the compounds and extracts in preparing pharmaceutical formulations and medicaments.

It is to be appreciated that certain aspects, modes, embodiments, variations and features of the invention are described below in various levels of detail in order to provide a substantial understanding of the present invention. The following terms are used throughout as described below, unless context clearly indicates otherwise.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the terms "congestive heart failure" (CHF), "chronic heart failure", "acute heart failure", and "heart failure" (HF) are used interchangeably, and refer to any condition characterized by abnormally low cardiac output in which the heart is unable to pump blood at an adequate rate or in adequate volume. When the heart is unable to adequately pump blood to the rest of the body, or when one or more of the heart valves becomes stenotic or otherwise incompetent, blood can back up into the lungs, causing the lungs to become congested with fluid. If this backward flow occurs over an extended period of time, heart failure can result. Typical symptoms of heart failure include shortness of breath (dyspnea), fatigue, weakness, difficulty breathing when lying flat, and swelling of the legs, ankles or abdomen (edema). Causes of heart failure are related to various disorders including coronary artery disease, systemic hypertension, cardiomyopathy or myocarditis, congenital heart disease, abnormal heart valves or valvular heart disease, severe lung disease, diabetes, severe anemia hyperthyroidism, arrhythmia or dysrhythmia and myocardial infarction. The primary signs of congestive heart failure are: cardiomegaly (enlarged heart), tachypnea (rapid breathing; occurs in the case of left side failure) and hepatomegaly (enlarged liver; occurs in the case of right side failure).

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds.

As used herein, the term "subject" refers to a mammal, such as a human, but can also be an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

As used herein, "substantially pure" means a composition or mixture is separated from components that naturally accompany it. Typically, the substance is substantially pure when it is at least 60%, by weight, free from the other naturally-occurring organic molecules with which it is naturally associated. In certain embodiments, the purity of the preparation is at least 75%, more preferably at least 90%, 95% and most preferably at least 99%, by weight. Methods for purification of the compounds to produce substantially chemically pure compounds are known to those of skill in the art. A substantially chemically pure compound may, however, be a mixture of stereoisomers. In such instances, further purification might increase the specific activity of the composition.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for heart failure if, after receiving a therapeutic amount of the aromatic-cationic peptides according to the methods described herein, the subject shows observable and/or measurable reduction in or absence of one or more signs and symptoms of heart failure, such as, e.g., cardiomegaly, tachypnea, and hepatomegaly. It is also to be appreciated that the various modes of treatment or prevention of medical conditions as described are intended to mean "substantial", which includes total but also less than total treatment or prevention, and wherein some biologically or medically relevant result is achieved. Treating heart failure, as used herein, also refers to treating any one or more of the conditions underlying heart failure, including, without limitation, decreased cardiac contractility, abnormal diastolic compliance, reduced stroke volume, pulmonary congestion, and decreased cardiac output.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. As used herein, preventing heart failure includes preventing the initiation of heart failure, delaying the initiation of heart failure, preventing the progression or advancement of heart failure, slowing the progression or advancement of heart failure, delaying the progression or advancement of heart failure, and reversing the progression of heart failure from an advanced to a less advanced stage.

Compositions of the Invention

The present invention provides methods of treating or preventing heart failure with extracts and compounds, and derivatives of such compounds from a variety of plants including *Geum japonicum*; Xian he cao (also known as *Agrimonia pilosa* Ledeb. (Rosaceae); and *Thymus mongolicus* Ronn (Lamiaceae), Herba Thymi or Mongolian Thyme Herb).

In some embodiments, the compound is a whole plant, an extract, e.g., an organic extract, of *Geum japonicum*, Xian he cao, *Agrimonia pilosa* Ledeb. (Rosaceae); and *Thymus mongolicus* Ronn (Lamiaceae). In a particular embodiment, the compound is a methanol/ethanol extract of *Geum japonicum* or an active fraction thereof. In some embodiments, the compound is a fraction of an extract of *Geum japonicum*.

The present invention provides methods of treating or preventing heart failure with agents and/or extracts and compounds, and derivatives of such compounds from a variety of plants including *Geum japonicum*. In some embodiments, the agent is an extract, e.g., an organic extract, of *Geum japonicum*. In a particular embodiment, the agent is a methanol/ethanol extract of *Geum japonicum* or an active fraction thereof. In certain embodiments, the agent is a tannin, including hydrolysable tannins such as Gemin A, B, C, D, E, and F or derivatives thereof. In other embodiments, the agent is a terpenoid such as e.g. ursolic acid, epimolic acid, maslinic acid, euscaphic acid, tormentic acid, 2-hydroxyursolic acid, 2,19-dihydroxy-ursolic acid, 2α,3β,19α,23-tetrahydroxy urs-12-en-28-oic acid, 2α,3β,19α,23-trihydroxy urs-12-en-23,28-dioic acid, and glucoside derivatives thereof such as Niga-ichigoside F1, Rosamultin, and Suavissimoside R1, or mixtures thereof.

In one embodiment, the triterpenoid polyphenol composition comprises: (i) one or more triterpenoids selected from the group consisting of: Asiatic acid, Niga-ichigoside F1, Kaji-ichigoside F1, Euscaphic acid, Asiaticoside, Tormentic acid, and Madecassic acid, and (ii) one or more polyphenols selected from the group consisting of: Gemin A, Casuarinin, Tellimagrandin II, Potentillin and ellagic acid. In one embodiment, the triterpenoid polyphenol composition comprises Asiatic acid, Niga-ichigoside F1, Kaji-ichigoside F1, Euscaphic acid, Asiaticoside, Tormentic acid, Madecassic acid, Gemin A, Casuarinin, Tellimagrandin II, Potentillin and ellagic acid.

The compound Nigiachigoside F1 can be found in various plant species. Most common plants: *Rubus coreanus; Combretum quadrangulare; Rubus imperialis; Rubus parvifolius; Aphloia theiformis; Desfontainia spinosa; Quercus ilex* L; *Rubus pinfaensis; Rubus suavissimus; Rubus* L. All Plants: *Acaena pinnatifida; Adinandra nitida; Anchusa officinalis* L; *Aphloia theiformis; Callicarpa bodinieri; Clematoclethra scandens; Combretum quadrangulare; Cyphotheca montan; Desfontainia spinosa; Folium ilicis* Purpureae; *Geum japonicum; Geum rivale; Geum rivale* L; *Ilex litseaefolia; Ilex oblonga; Ilex purpurea; Japanese butterbur; Margyricarpus setosus; Paradrymonia macrophylla; Polylepis incana* (Rosaceae); *Prunella vulgaris; Prunus serrulata* var *spontanea; Quercus acutissima* Carruthers; *Quercus cerris* L; *Quercus dentata* Thunb.; *Quercus glauca; Quercus ilex* L; *Quercus imbricaria; Quercus laurifolia* Michx; *Quercus suber* L; *Quercus virginiana; Rosa laevigata* Michx; *Rosa laevigata* michx; *Rosa multiflora; Rosa multiflora* Thunb.; *Rosa transmorrisonensis; Rubi fructus* (Bogbunja); *Rubus alceaefolius* Poir; *Rubus alleghaniensis; Rubus amabilis; Rubus coreanus; Rubus coriifolius; Rubus crataegifolius; Rubus imperialis; Rubus imperialis* (Rosaceae); *Rubus* L; *Rubus parvifolius; Rubus pinfaensis; Rubus sanctus*; Schreber; *Rubus* species; *Rubus suavissimus; Rubus xanthocarpus; Salvia tricupis; Sanguisorba hakusanensis; Sanguisorba minor; Sanguisorba officinalis; Sarcopoterium spinosum; Strasburgeria robusta; Syzygium levinei; Verbascum wiedemannianum; Vochysia divergens*; and *Vochysia pacifica.*

The compound Rosamultin can be found in various plant species. Most Common Plants: *Rosa multiflora* Thunb.; *Rosa rugosa; Combretum quadrangulare; Musanga cecropioides; Potentilla anserine; Rhaponticum uniflorum*; and *Rubus* L. All Plants: *Acaena magellanica; Acaena pinnatifida; Actinidia arguta; Adinandra nitida; Agrimonia pilosa; Albizzia julibrissin* Durazz; *Anchusa strigosa; Aphloia theiformis; Campylotropis hirtella* (Franch Schindl); *Combretum quadrangulare*; Daxueteng (*Caulis sargentodoxae*); *Dichotomanthes tristaniaecarpa; Diospyros kaki* L; *Duchesnea indica* Focke; *Geum japonicum; Ilex litseaefolia; Ixora finlaysoniana; Licania licaniaeflora; Licania pyrifolia; Margyricarpus setosus; Musanga cecropioides; Petasites japonicus; Pimpinella magna; Potentilla anserina* L; *Potentilla anserine; Potentilla erecta; Potentilla erecta* L Rhizomes; *Potentilla griffithii* var *velutina; Rhaponticum uniflorum; Rosa davurica; Rosa laevigata; Rosa multiflora; Rosa multiflora* Thunb.; *Rosa rugosa; Rosa rugosa; Rosa sterilis; Rosa taiwanensis; Rosa transmorrisonensis*; Rosamultin; *Rubi fructus* (Bogbunja); *Rubus* L; *Rubus sanctus* Schreber; *Rubus* species; *Salvia tricupis; Sanguisorba alpina; Sanguisorba minor; Sanguisorba officinalis; Sarcopoterium spinosum; Sargentodoxa cuneata; Terminalia argentea; Verbascum wiedemannianum*; and *Vitex altissima.*

The compound 2α,3β,19α23tetrahydroxy urs-12-en-28-oic acid can be found in various plants. Most Common Plants: *Rubus coreanus; Combretum quadrangulare; Desfontainia spinosa; Campsis grandiflora; Myrianthus arboreus; Quercus ilex* L; *Rosa laevigata* Michx; *Rubi fructus; Rubus* L; *Rubus pinfaensi*; and *Rumex japonicus.* All Plants: *Actinidia deliciosa* cv Golden King; *Actinidia indochinensis; Anchusa officinalis* L; *Campsis grandiflora; Centella asiatica; Centipeda minima; Clematoclethra scandens; Coleus amboinicus* Loureiro; *Coleus forskohlii; Combretum quadrangulare; Cussonia bancoensis; Desfontainia spinosa; Epilobium hirsutum* L; *Eriobotrya japonica; Gambeya boukokoensis; Geum japonicum; Hyptis capitata; Ilex purpurea*; Labiatae plants; *Lagerstroemia speciosa; Lobelia longisepala; Madhuca pasquiery; Miconia trailii; Myrianthus arboreus; Ocotea suaveolens; Paradrymonia macrophylla; Pimpinella magna; Planchonella duclitan* Bakhuizan; *Polylepis incana; Pourouma guianensis; Quercus acutissima* Carruthers; *Quercus ilex* L; *Quercus laurifolia* Michx; *Quercus virginiana; R koehneanus; R medius; R microphyllus; R trifidus; Rhododendron japonicum; Rosa laevigata* Michx; *Rosa laevigata* Michx; *Rosa laevigatae; Rosa multiflora; Rosa transmorrisonensis; Rubi fructus; Rubus buergeri; Rubus coreanus; Rubus ellipticus; Rubus imperialis; Rubus* L; *Rubus pinfaensis; Rubus pungens* Camb var *oldhamii; Rubus sanctus* Schreber; *Rumex japonicus; Sanguisorba minor; Sarcopoterium spinosum*; Strawberry cv Houkouwase; *Symplocos chinensis; Symplocos paniculata; Symplocos spicata; Syzygium levinei; Vochysia divergens*; and *Vochysia pacifica.*

The compound Suavissimoside can be found in various plants. Most Common Plants; *Rubus parvifolius; Rhaponticum uniflorum; Sanguisorba officinalis*; and *Rubus* L. All Plants: *Chaenomeles sinensis; Geum japonicum; Ilex aculeolata; Ilex godajam; Ilex rotunda* Thunb.; *Pedicularis resupinata oppositifolia; Quercus glauca; Quercus robur stenocarpa; Rhaponticum uniflorum; Rubus alceaefolius* Poir; *Rubus cochinchinensis; Rubus coreanus; Rubus crataegifolius; Rubus* L; *Rubus parviflorus; Rubus pileatus; Rubus sanctus* Schreber; *Rubus suavissimus; Sanguisorba officinalis*; and *Trachelospermum asiaticum.*

The compound Tormentic (Euscaphic) Acid can be found in various plants. Most Common Plants: *Eriobotrya japonica; Rosa multiflora* Thunb.; *Musanga cecropioides; Chaenomeles sinensis; Myrianthus arboreus; Perilla frutescens; Rosa rugosa; Acanthochlamys bracteata; Agrimonia pilosa; Chaenomeles sinensis* Koehne; *Duchesnea indica; Potentilla multifida* L; *Rhaponticum uniflorum; Rosa laevigata; Rosa laevigata* Michx; *Rubus chingii; Rubus* L; *Rumex japonicus*; and *Sanguisorba officinalis.* All Plants: *C. olitorius* (jute plant); *Acaena pinnatifida; Acanthochlamys bracteata; Agrimonia pilosa* Ledeb; *Anchusa strigosa; Ardisia japonica; Arnebia euchroma; Asparagus filicinus*; Bonpl; *Callicarpa bodinieri* (II); *Campsis grandifiora; Campylotropis hirtella* (Franch Schindl); *Cecropia lyratiloba miquel; Chaenomeles sinensis; Chaenomeles sinensis* (Thouin) Koehne; *Chaenomeles sinensis* Koehne; Cili (*Rosa roxburghii*); *Coleus amboinicus* Loureiro; *Coleus forskohlii; Coleus spicatus; Corchorus capsularis; Cotoneaster simonsii; Cowainea mexicana; Crataegus pinnatifida* var *psilosa; Cunila lythrifolia; Debregeasia salicifolia; Dichondra repens* Forst; *Diuranthera inarticulata; Duchesnea indica; Duchesnea indica* Focke; *Elsholtzia bodinieri; Elsholtzia herb; Epilobium hirsutum* L; *Eriobotrya deflexa; Eriobotrya japonica; Eriobotrya japonica calli; Eriobotrya japonica* L; *Eriobotrya japonica* Lindl; *Eriope blanchetii; Euscaphis japonica; Fructus ligustri lucidi; Geum rivale*; Goreishi; *Hoslundia opposita* (Lamiaceae); *Hyptis capitata; Isodon loxothyrsus; Isodon oresbius; Jacaranda caucana* Pittier (Bignoniaceae); *Lagerstroemia speciosa; Lepechinia caulescens; Leucoseptrum stellipillum; Licania pyrifolia; Lycopus lucidus; Margyricarpus setosus; Marsypianthes chamaedrys; Mentha citrata; Musanga cecropioides; Myrianthus arboreus; Myrianthus serratus; Nepeta prattii; Ocimum basilicum; Paliurus hemsleyanus; Paradrymonia macrophylla; Perilla frutescens; Phlomis umbrosa; Physocarpus intermedius; Pimpinella magna; Polylepis incana* (Rosaceae); *Potentilla anserina* L; *Potentilla discolor; Potentilla fruticosa; Potentilla griffithii* var *Velutina; Potentilla multifida* L; *Potentilla multifida* L (Rosaceae); *Potentilla tormentilla; Poterium ancistroides; Pourouma guianensis; Prunella* Linn; *Prunella vulgaris; Prunus zippeliana; Pygeum acuminatum* Coleb; *Pygeum topengii; Pyrus calleiyana decne; R multibracteata; Rabdosia effusa* Hara; *Rabdosis* (Blume) Hasskarl; Relhania; *Rhaponticum uniflorum; Rosa bella; Rosa davidii; Rosa davurica; Rosa laevigata; Rosa laevigata* Michx; *Rosa multiflora; Rosa multiflora* Thunb.; *Rosa rugosa; Rosa sericea; Rosa soulieana; Rosa sterilis; Rosa taiwanensis; Rosa transmorrisonensis; Rubus alceaefolius* Poir; *Rubus buergeri; Rubus chingii; Rubus cochinchinensis; Rubus ellipticus* Smith; *Rubus innominatus; Rubus irenaeus; Rubus* L; *Rubus moluccanus* (Rosaceae); *Rubus parkeri* root; *Rubus pinfaensis; Rubus pungens* Camb var *oldhamii; Rubus sieboldii; Rubus* species; *Rubus swinhoei; Rubus xanthocarpus; Rumex japonicus; S glabrescens; Sabia parviflora* Wall ex Roxb; *Salvia broussonetii; Salvia japonica; Salvia paramiltiorrhiza; Salvia roborowskii* Maxim; *Salvia tricupis; Salvia trijuga* Diels; *Sanguisorba officinalis*; Sanguisorbeae; *Schnabelia tetradonta; Spiraea prunifolia* var *simpliciflora; Synurus excelsus; Tecoma mollis* Humb; *Ternstroemia gymnanthera* Callus; *Tiarella polyphylla; Toddalia asiatica; Turpinia arguta* leaf; *Verbena officinalis; Vismia guineensis*; and *Vitex altissima.*

Preparation of Organic Extract of *Geum japonicum*

A method for preparing an organic extract from *Geum japonicum* is provided. This method comprises the step of (a) extracting the plant of *Geum japonicum* with alcohol selected from the group consisting of C1-C4 alcohols. This step maybe repeated 3-6 times, typically 5 times, at room temperature. Before performing step (a), the plant material may be powdered. The C1-C4 alcohols include methanol, ethanol, n-propanol, iso-propanol, n-butanol, iso-butanol, and ter-butanol. Typically, alcohol is added in 1-10 times by weight of the amount of the *Geum japonicum* to be extracted.

The methods may further comprise the step of (b) drying the extract obtained from the step of (a) into a dried powder; and (c) successively extracting the powder obtained from the step of (b) with C6 alkane, EtOAc and an alcohol selected from the group consisting of C1-C4 alcohols. The C6 alkane includes cyclic and non-cyclic alkane having 6 carbon atoms, including, for example, cyclohexane, n-hexane, and neo-hexane, etc. The C1-C4 alcohols include methanol, ethanol, n-propanol, iso-propanol, n-butanol, iso-butanol, and ter-butanol. The amount of organic solvent to be used is typically 1-10 times by weight of the amount of the powders to be further extracted.

The method as recited above may also include filtering the extract to remove any insoluble powders therein. A drying step may be completed under reduced pressure at a temperature higher than room temperature, for example, at 50° C.

In one embodiment, the extracts, fractions, and compounds of the invention are obtained by extraction, using water and/or of an organic solvent, from crude plant material comprises the following stages:

1. Extraction by addition to the plant material, of water and/or of organic solvent(s), by subjecting the whole to a treatment such as maceration/lixiviation, ultrasonics or microwaves;
2. Delipidation before or after the extraction stage using a solvent of petroleum ether, hexane or chloroform type;
3. Optionally, additional extraction of the extract recovered by an organic solvent of ethyl acetate or ethyl ether type,
4. Optionally, concentration of the crude extract obtained, and, if desired, its lyophilization.

According one aspect, considering the enrichment that it allows to be attained, the crude extract may be subjected to a purification stage by chromatography. In one embodiment, centrifugal partition chromatography (CPC) is used. This technique is in particular described by A. P. FOUCAULT, Ed., Centrifugal Partition Chromatography, Chromatographic Science Series, Marcel Dekker Inc., 1995, 68, or W. D. CONWAY, Ed., Countercurrent Chromatography apparatus theory and applications, VCH Publishers Inc., 1990. CPC is based on the partition of the solutes between two non-miscible liquid phases prepared by the mixture of two or more solvents or solutions. One of the two phases is kept stationary by a centrifugal force. The solvents, their proportions and the flow rate chosen closely depend both on the stability of the stationary phase within the CPC column and the actual pressure.

A person skilled in the art will therefore choose the most appropriate solvent or solvents depending on the nature of the purified extract desired. These different extracts, namely crude or enriched also fall within the scope of the invention. The implementation of additional separation stages allows isolation of these extracts enriched with one or more compounds. These separations can be carried out on fractions enriched from a crude extract or on the crude extract itself by using mixtures of appropriate solvents according to the proportions which are suitable for the sought separation.

Methods and Compositions for the Prevention or Treatment of Heart Failure

Heart failure (HF) is a compilation of signs and symptoms, all of which are caused by an inability of the heart to appropriately increase cardiac output during exertion. HF may be caused by chronic hypertension, ischemia, tachyarrhythmias, infarct or idiopathic cardiomyopathy. The cardiac diseases associated with symptoms of congestive failure include dilated cardiomyopathy, and hypertrophic cardiomyopathy. The classical symptoms of the disease include shortness of breath, edema, and overwhelming fatigue. As the disease progresses, the lack of cardiac output may contribute to the failure of other body organs, leading to cardiogenic shock, arrhythmias, electromechanical dissociation, and death.

In one aspect, the present technology relates to the treatment or prevention of heart failure by administration of a composition of triterpenoids and polyphenols (TPs). The present inventors found TPs had significant protective effects on cultured fetal cardiac myocytes against stresses including hypoxic stress (hs), prenately stress (ps), and cardiac toxin (ct). Further studies with sub-clinical HF animal models demonstrated that TPs could provide effective treatment of HF in animal models derived from myocardial infarction. Furthermore, the effective treatment of HF in animal models has been successfully translated into an effective treatment in human HF patients that experienced prior heart infarction, hypertension and chronic coronary heart disease.

In accordance with one aspect, the present invention relates to a composition of natural compounds comprised of triterpenoids and polyphenols for the treatment of HF. Suitable triterpenoids include, but are not limited to, Asiatic acid, Niga-ichigoside F1, Kaji-ichigoside F1, Euscaphic acid, Asiaticoside, Tormentic acid, Madecassic acid and the preferred polyphenols are Gemin A, Casuarinin, Tellimagrandin II, Potentillin and ellagic acid.

In one aspect, the methods for the prevention or treatment of HF include administering to a mammal in need thereof agents, active fractions, and/or extracts and compounds, and derivatives of such compounds from a variety of plants including *Geum japonicum, R. imperialis, Vochysiapacifica, Rubus coreanus, Rubus allegheniensis, Rubus parviforlius* L., *Agrimonia pilosa, Potentilla kleiniana, Coriaria japonica*, and grape seeds. In some embodiments, the extract is an organic extract obtained from the plant *Geum japonicum*. In certain embodiments, the agent is a methanol/ethanol extract of *Geum japonicum* or an active fraction thereof. Exemplary agents include tripterpenoids and polyphenols, including hydrolysable tannins such as Gemin A, B, C, D, E, and F or derivatives thereof. In other embodiments, the agent is a terpenoid such as e.g. ursolic acid, epimolic acid, maslinic acid, euscaphic acid, tormentic acid, 2-hydroxyursolic acid, 2,19-dihydroxy-ursolic acid, 2α,3β,19α,23-tetrahydroxy urs-12-en-28-oic acid, 2α,3β,19α,23-trihydroxy urs-12-en-23,28-dioic acid, and glucoside derivatives thereof such as Niga-ichigoside F1, Rosamultin, and Suavissimoside R1, or mixtures thereof.

In another aspect, an agent for the treatment or prevention of heart failure is part of a pharmaceutical composition containing one or more excipients, carriers, or fillers. In one embodiment, the pharmaceutical composition is packaged in unit dosage form. The unit dosage form is effective in improving cardiac output, shortness of breath, edema, and fatigue in the subject.

In some embodiments, in vivo models of heart failure are used to assess the effects of an agent on a subject. Suitable in vivo models include coronary ligation in rats, and a toxic cardiomyopathy model, which includes the administration of doxorubicin or anthracycline to an animal subject. The effects of the agent in mediating the heart failure in the animal subject are investigated and compared to suitable controls.

Formulations and Dosages of Pharmaceutical Compositions.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, modulating compounds may be administered to farm animals to improve their ability to withstand farming conditions longer.

In various embodiments of the invention, suitable in vitro or in vivo assays are performed to determine the effect of an agent (extracts, fractions and compounds) of the invention and whether its administration is indicated for treatment of the affected disease or medical condition in a subject. Examples of these assays are described above in connection with a specific disease or medical treatment.

Typically, an effective amount of the compositions of the present invention, sufficient for achieving a therapeutic or prophylactic effect, range from about 0.001 mg per kilogram body weight per day to about 10,000 mg per kilogram body weight per day. Suitably, the dosage ranges are from about 0.01 mg per kilogram body weight per day to about 1000 mg per kilogram body weight per day. For administration of an agent, the dosage ranges may be from about 0.01 to 1000 mg/kg, and more usually 0.1 to 500 mg/kg every day, every two days or every three days, of the host body weight. An exemplary treatment regime entails administration once every two days or once a week or once every month. The agent is usually administered on multiple occasions. Intervals between single dosages can be daily, weekly, monthly or yearly. Alternatively, the agents can be administered as a sustained release formulation, in which case less frequent administration is required. Dosage and frequency vary depending on the half-life of the agent in the subject. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

Toxicity. Suitably, an effective amount (e.g., dose) of an agent described herein will provide therapeutic benefit without causing substantial toxicity to the subject. Toxicity of the agent described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the agent described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

According to the methods of the present invention, the agents can be incorporated into pharmaceutical compositions suitable for administration. In some embodiments, the pharmaceutical compositions may comprise purified or substantially purified TPs and a pharmaceutically-acceptable carrier in a form suitable for administration to a subject. In other embodiments, the pharmaceutical compositions may comprise pharmaceutically-acceptable carriers are determined in part by the particular composition being administered, as well as by the particular method used to administer the composition. Accordingly, there is a wide variety of suitable formulations of pharmaceutical compositions for administering the compositions (see, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. A person of ordinary skill in the art, would have no difficulty determining the appropriate timing, sequence and dosages of administration for particular drugs and compositions of the present invention.

Suitable examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the agent, use thereof in the compositions is contemplated. Supplementary active compounds can also be incorporated into the compositions.

A pharmaceutical composition of the invention is formulated to be compatible with its intended route of administration. The compositions of the present invention can be administered by parenteral, topical, intravenous, oral, subcutaneous, intraarterial, intradermal, transdermal, rectal, intracranial, intraperitoneal, intranasal; intramuscular route or as inhalants. The agent can optionally be administered in combination with other agents that are at least partly effective in treating various diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the agents in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of this invention can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, the agents are prepared with carriers that will protect the agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

EXAMPLES

The present technology is further illustrated by the following examples, which should not be construed as limiting in any way.

Example 1

Identification of the Active Composition of Compounds with Dual Actions on Protection of Cardiac Myocytes Against Stresses and Improvement of Myocardial Blood Perfusion A bio-assay guided isolation strategy was used for screening natural constituents to identify the composition of compounds showing dual actions on protection of cardiac myocytes against stresses and improvement of myocardial blood perfusion. Rat neonatal cardiac myocyte primary culture and HF rat model derived from gross myocardial infarction were used as the bio-assay systems.

Plant Material. The whole plants of *Geum Japonicum* Thunb. var. *chinense* and *Centella Asiatica* were collected from Guizhou Province in September 2007. A voucher specimen was deposited with the School of Chemical Biology and Pharmaceutical Science of Capital University of Medical Science, China and the Laboratory of Innovative Medicine, Hong Kong.

Extraction and Isolation. The air-dried whole plants of *Geum Japonicum* Thunb. var. *chinense* (3.5 kg) and *Centella Asiatica* (1.5 kg) were cut into small pieces and macerated with 20 liter methanol at room temperature for a week (3 times). After evaporation of, solvent in vacuo, the residue (510 g) was recovered. It was found that this extract displayed the dual actions on protection of cardiac myocytes against stresses and improvement of myocardial blood perfusion. The bioassay guided composition analysis demonstrated that the active compounds are mainly belonged to two groups of compounds (polyphenols and triterpenoids) consisting of: Gemin A, Casuarinin, Tellimagrandin II, Potentillin, ellagic acid, Niga-ichigoside F1, Kaji-ichigoside F1, Euscaphic acid, Asiaticoside, Tormentic acid, and Madecassic acid.

The sub-composition containing triterpenes was found to protect cardiac myocytes against hs, ps and ct stresses when the triterpenes fraction (30 μg/ml) were applied to the neonatal cardiac myocyte cultures. Another sub-composition of polyphenols was identified to significantly increase blood perfusion of the failure hearts when the polyphenol fraction (100 mg/kg/daily for 2 weeks) was intragastricly administered to MI induced heart failure rat models. Liquid chromatography coupled to mass spectrometry and nuclear magnetic resonance spectroscopy was used for determinations of the identities of the major bio-active compounds contained in both sub-compositions. It was found that the sub-composition, which showed protective effect on cardiac myocytes, contained mainly triterpenoids including Asiatic acid, Niga-ichigoside F1, Kaji-ichigoside F1, Euscaphic acid, Asiaticoside, Tormentic acid, Madecassic acid. It was found that the natural ratio of the two groups of compounds from the methanol extract of *Geum japonicum* and *Centella Asiatica* is active for the treatment of HF.

Example 2

A Composition of TPs Protected Cultured Neonatal Cardiomyocyes

In vivo, loss of ventricular myocytes by apoptosis leads to heart failure. Over-expression of pro-apoptotic signals and/or down-regulation of anti-apoptotic (survival) signals in cells are closely involved in HF development processes. Substances that can enhance survival or prevent apoptotic death in cardiomyocytes could be candidates for potential therapeutic usefulness in the treatment of HF. Therefore, we tested whether TPs could enhance the survival potential or prevent cell death in cultured neonatal cardiac myocytes. Primary myocyte cultures were obtained from 1 day old neonatal rat. The neonatal rat cardiac myocyte suspensions with 25,000 cells/ml were made in DMEM containing 10% bovine calf serum (BCS) and 1% glutamine-penicillin-streptomycin (GPS) and placed onto 24-well culture plates and incubated at 37° C. for 24 hours. The medium was then replaced with 0.5 ml DMEM, 5% BCS, and the test sample (10 μl 5% DMSO containing 50 μg TPs) was applied to each well. The same volume of 5% DMSO was used for the control. Cultures were maintained at 37° C. and 5% $CO_2$ for 24, 48 and 72 hours respectively. The cultured cardiac myocytes, which was subjected to hypoxia by incubation in an environmental chamber, were tested. The chamber oxygen concentration was maintained at 10 mmHg for 24 hours. It was shown that TPs (50 μg/ml) treatment of the cultured cardiac myocytes during the period of the hypoxia significantly increased the expression of some cell survival factors, such as Akt1, BCL2 and EGF, and prevented cell death against hypoxia compared with the vehicle-treated control myocytes. The apoptotic cells increased with prolonged hypoxia in the vehicle-treated control cardiac myocytes. By contrast, TPs treatment inhibited the activation of caspase 3, 7 and decreased apoptotic cells ($P<0.01$).

Example 3

A Composition of TPs Induced Therapeutic Effects in an HF Animal Model

Myocardial ischemia or infarction is a common risk factor for the development of congestive HF in humans. The ischemic or infarcted hearts undergo persistent left ventricular remodelling including changes in geometry, structure, and function. Persistent remodelling, although initially adaptive, ultimately precipitates the progression of HF. The most common causes of HF are myocardial infarction, hypertension, and chemotherapy-induced myocardial damage. Therefore, we initially tested the therapeutic effects of TPs in a HF animal model, which was developed from myocardial infarction.

Since myocardial infarction (MI) is one of the most common causes of HF, the model of MI-induced congestive HF was used to evaluate the treatment effect of TPs. Rat models of HF secondary to MI are useful in studying the progression of cardiac dysfunction and in testing therapeutic approaches. In the present example, we developed a model of HF utilizing SD rats. Permanent ligation of the left anterior descending coronary artery (LAD) was used to produce a gross infarct in the LV. Using this rat model, we further studied the course of LV dysfunction and enlargement from 1 to 8 weeks post ligation. Due to ischemia of the hearts, ST segment of ECG was significantly lowered, implying ischemia of the ventricle (FIG. 1). LV ejection fraction (EF) ranged between 56-68% in control rats; after ligation of LAD, EF decreased to 48±6% at 1 week, 38±5% at 2 week, 36±4% at 4 weeks, 29±3% at 8 weeks ($P<0.001$, ligated vs. sham). LV end-diastolic volume (LVEDV) in sham-operated rats ranged between 0.36-0.45 ml. It increased to 0.63±0.03, 0.69±0.05, 0.76±0.06, and 0.81±0.07 ml at week 1, 2, 4, and 8 after MI, respectively ($P<0.001$ vs. sham). LV end-diastolic pressure was significantly elevated at all time points.

Figure 2:
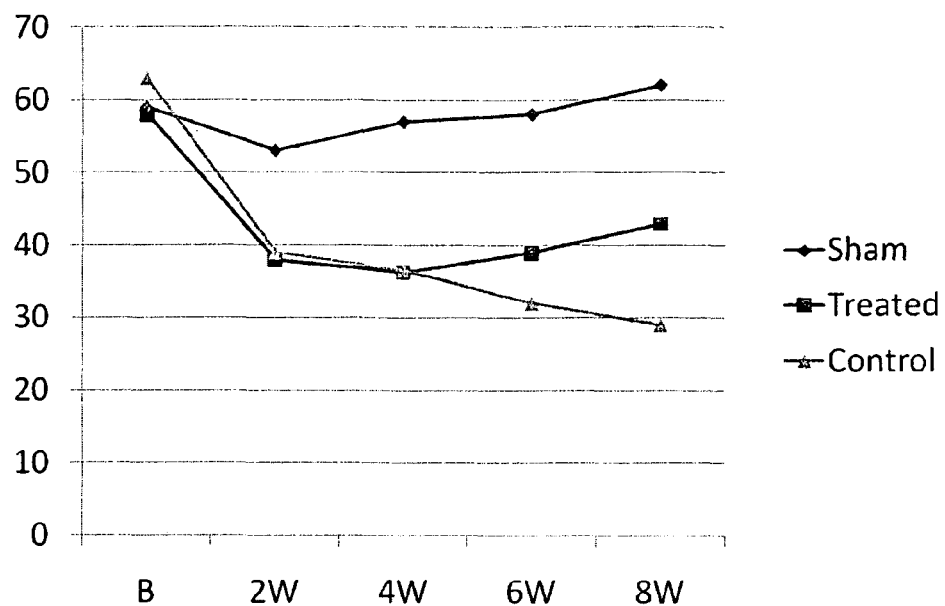
FIG. 2 presents data showing that TPs treatment mediated improvements of heart function. Sham denotes the open chest surgery without ligation of LAD. B, Before ligation of the LAD. 2 W, 2 weeks post ligation. The LVEF values in both groups of rats (Treated & Control) significantly declined. 4 W, 4 weeks post ligation, the LVEF further declined resulting in HF. The treatment with TPs started right after this measurement of echocardiography. 6 W, 6 weeks post-ligation and 2 weeks TPs treatment with LVEF increased by 20%. 8 W, 8 weeks post-ligation and 4 weeks post-TPs treatment. The LVEF was further improved. In comparison, the LVEF progressively declined in vehicle-treated control hearts (Control).

The TPs (300 mg/kg, daily) dissolved in 5% DMSO (0.5 ml) was introgastricly administered to the MI rats 4 weeks post-ligation, daily for 4 weeks with equivalent amount of 5% DMSO to the control vehicle-treated MI rats. For sham-operated rats (n=8), thoracotomy was performed without LAD ligation. It was found that 3-4 weeks TPs treatment significantly restored the lowered ST segment of the ECG due to ischemia (FIG. 1) and improved the heart functional performance. In that the significantly increased LVEDV (0.763±0.06 ml) and decreased cardiac output (96±12 ml/min/kg) were restored to 0.58±0.03 ml and 172±16 ml/min/kg respectively. The significantly decreased EF was increased from 36.3±5% before treatment to 42.3±3.9%, after 4 weeks TPs treatment (FIG. 2). By contrast, in the vehicle-treated control, the LVEDV increased to 0.83±0.08 ml and EF decreased to 28.6±3.9% respectively (FIG. 2) ($P<0.001$ vs. the TPs-treated).

Figure 3:
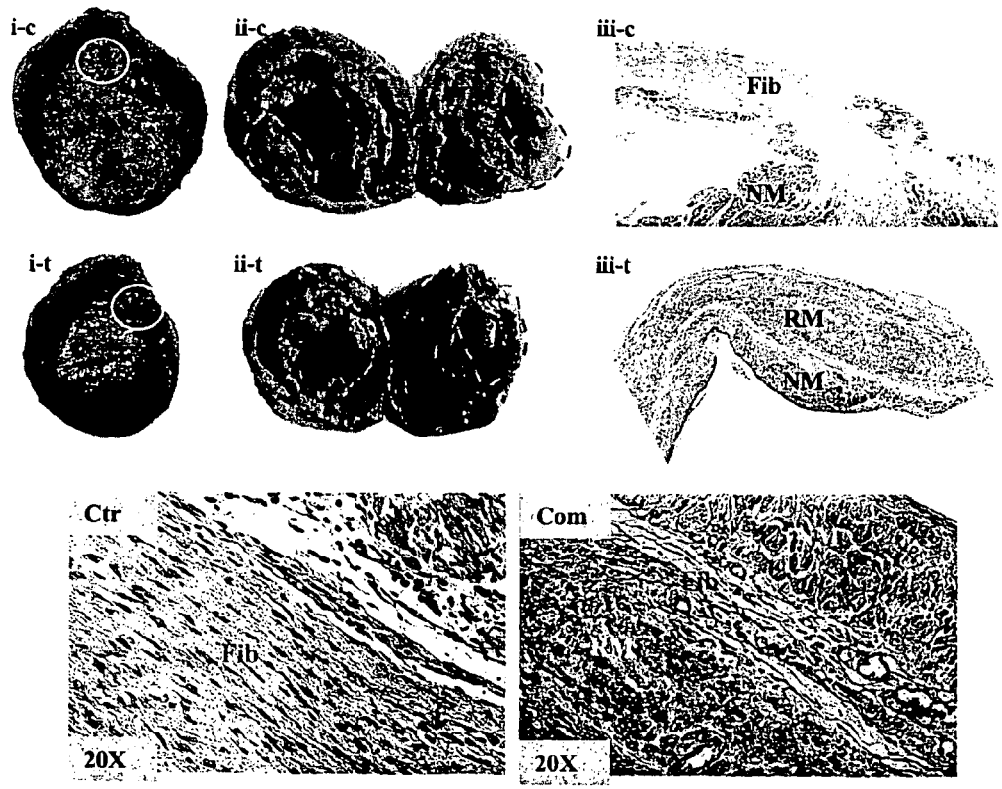
FIG. 3 shows histological analysis of the HF. i-c, The vehicle treated control hearts, the left ventricle appeared pale, large, and baggy. i-t, The appearance of the TPs treated heart appeared red and compacted. ii-c, The thin and pale LV anterior wall and enlarged ventricle were found (the dashed line circled). iit, The infarcted area of LV in TPs treated heart appeared red and thicker (dashed line circled). iii-c, The fibrous replacement in infarcted area of vehicle treated hearts (Fib). iii-t, Neovascularization and myocardial regeneration (RM) were observed replacing the infarcted heart tissues. Ctr, The whole infarcted regions of the vehicle treated hearts were replaced by the blue stained fibrous scar by Masson trichrome staining. Com, In comparison, the infarct area was significantly smaller and the replacement of the infarcted myocardium with newly regenerated heart tissues was found (RM) in TPs treated group.

Animals were sacrificed after final echocardiography measurements on week 8 post ligation. The hearts of the sacrificed rats were removed and washed with PBS. The vehicle treated control hearts, especially the left ventricle, appeared white, large, and baggy. By contrast, the appearance of the TPs-treated heart appeared red and compacted (FIG. 3). All the specimens harvested were either sectioned for histological and immunohistochemical analyses or used for Western blot and DNA microarray studies. It was observed that the infarcted area of LV in TPs treated heart appeared red and the infarcted left anterior wall is thicker in comparison with the thin and white LV anterior wall in vehicle-treated heart. For histological examination, the left ventricles were removed and cut from apex-to-base in 3 transverse slices and embedded in paraffin. The infarct size and vascular density in the LV were measured accordingly. It was found that the infarct area was significantly larger and the wall thickness of LV was significantly thinned in vehicle treated group (FIG. 3) with the whole region of the infarct replaced by the blue stained fibrous scar by Masson trichrome staining (FIG. 3). In comparison, the infarct area was significantly smaller and the heart left ventricle anterior wall was thicker and appeared red in TPs treated group (FIG. 3). Histological analysis also showed the replacement of the infarcted myocardium with the newly regenerated heart tissues in TPs treated group (FIG. 3). To quantify the average number of capillaries in LV, 6 sections from each transverse slice, in total 18 sections from the 3 slices of each heart were analyzed. It was found that the average capillary density of LV in TPs treated hearts was significantly higher than that in the vehicle-treated (FIG. 3) ($P<0.01$).

Example 4

A Composition of TPs had Therapeutic Effects for HF in Human Subjects

Figure 4:
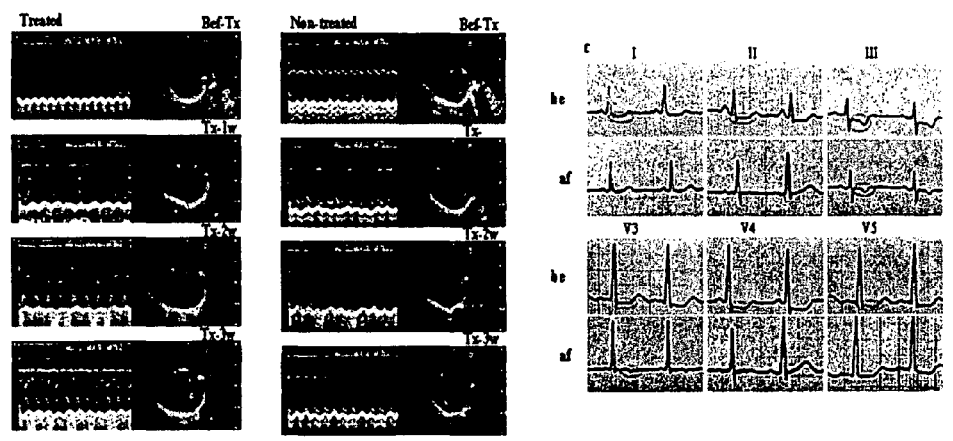
FIG. 4 is an evaluation of the therapeutic effects of TPs on HF patients. Echocardiography examination demonstrated that the global LV function also significantly improved with 25-94% of LV ejection fraction (EF) and 31-100% of fraction shortening (FS) restored. The average thickness of the thinned LV walls (5.5 mm) due to enlargement of LV restored to average 8 mm with significantly improved LV blood perfusion (SPECT) and restored ST segments in ECG.

This example tested the effect of TPs containing extract obtained from *Geum japonicum* and *Centella Asiatica* in humans in a clinical setting. Our preliminary clinical trials demonstrated that after 4 weeks oral administration of the extract (2 gram/day) to the patients (6 patients both male and female with their full awareness and written consent) who had known heart disease, such as heart infarction, hypertension and chronic coronary heart disease, with a history of HF. Two weeks after treatment, all patients reported significant improvements in the symptoms of HF, such as dizziness, lower leg edema, fatigue, nausea, coughing, at rest. Echocardiography examination demonstrated that the global left ventricle (LV) function significantly improved with 30-61% of LV ejection fraction (EF) and 21-76.9% of fraction shortening (FS) restored. The average thickness of the thinned LV walls (6.2 mm) due to enlargement of LV restored to average 7.7 mm with significantly improved wall motion (FIG. 4 & Table 1).

In an exercise tolerance test, the induction of chest suppression before treatment was from sedentary to climbing 6-10 steps, but 50-60 steps climbing did not induced chest suppression in these patients 2-4 weeks post treatment (Table 2). The impressive improvements in symptoms and echocardiography measurements were not observed in other patients with similar HF receiving conventional treatment in the same hospital. These results indicated that administration of TPs containing extract remarkably improved the symptoms of HF, which did not respond well to the conventional treatment modality in the patients examined, and that the improvements of HF may be maintained for months or years.

Figure 5:
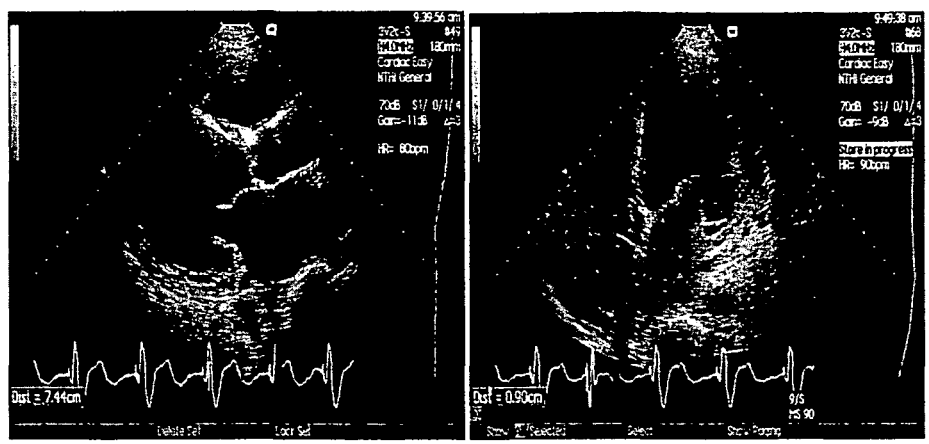
FIG. 5 shows the echocardiography of a severe HF patient due to multi-heart attacks. Before treatment, the left ventricle diameter (LVD) was extremely enlarged up to 170.8×78.3 mm. The left ventricle wall thickness was thinned (6.7 mm) and the LVEF was extremely low (8%) due to severe HF. However, after 4 weeks treatment with the drug, the LVD was significantly restored to 72×70 mm; the thickness of left ventricle wall was restored to 8 mm and the LVEF was 260% increased to 21%.
Figure 5:
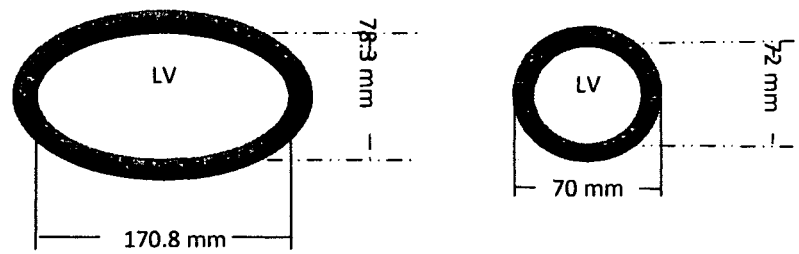

The therapeutic effects of the TPs extract on a severe heart failure patient were examined. A male patient had severe heart failure at the end stage of his illness at the time of examination. He had repeated heart infarction, hypertension and recurrent HF and was under cardiac pacing. His heart was extremely enlarged (the left ventricle diameter: 170.8×78.3 mm) due to HF (FIG. 5) and more than 80% of his heart was insufficiently perfused (FIG. 5). His heart function extremely declined with LVEF about 8%. However, 4 weeks treatment with the drug (2 gram/day), the left ventricle diameter was significantly restored to 72×70 mm and the LVEF was 260% increased to 21%.

In an exercise tolerance test, the induction of chest suppression before treatment was from sedentary to slow walking or climbing 3-6 steps, but 20 steps climbing did not induce chest suppression in this patient after 4 weeks treatment of the TPs containing extract. The impressive improvements in symptoms and echocardiography measurements were not observed in other similar patients receiving conventional treatment in the same hospital. These results indicated that administration of TPs containing extract remarkably improved the symptoms of HF, which did not respond well to the conventional treatment, and that the improvements of HF may be maintained for months or years.

TABLE 1

Evaluation of left ventricle function in patients (n = 6)

| Exercise tolerance test | Before treatment 5-10 steps induced chest suppression | After treatment 50-60 steps induced no chest suppression |
|---|---|---|
| LVPWT (mm) | 6.2 | 7.7 |
| LVIDd (mm) | 71 | 57 |
| IVIDs (mm) (n = 3) | 62 | 43 |
| LVEDV (ml) (n = 3) | 256 | 173 |
| LVESV (ml) (n = 3) | 173 | 98 |
| SV (ml) (n = 3) | 61 | 75 |
| EF (%) (n = 3) | 28 | 45 |
| FS (%) (n = 3) | 13 | 23 |

TABLE 2

Therapeutic effects on Heart Disease Patients

| Symptoms | Before treatment | After treatment |
|---|---|---|
| Dyspnea | ++ - - - +++ | - - - - + |
| Dizziness | ++ - - - +++ | - - - - + |
| Edema | ++ - - - +++ | - - - - + |
| Blood hyper-viscous | +++ - - - ++++ | - - - - + |
| Fatigue | ++ - - - ++++ | + - - - ++ |
| Heart enlargement | ++ - - - ++++ | + - - - ++ |
| Coughing | ++ - - - +++ | - - - - + |
| Chest suppression | ++ - - - +++ | - - - - + |

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCES

Heart Disease and Stroke Statistics—2007 Update, Heart Disease and Stroke Statistics—2007 Update, A Report From the American Heart Association Statistics Committee and Stroke Statistics Subcommittee.

British Heart Foundation. *European Cardiovascular Disease Statistics;* 2000. Edition.

Ho K K L, Anderson K M, Kannel W B, Grossman W, Levy D. Survival after the onset of congestive heart failure in Framingham heart study subjects. *Circulation* 1993; 88:107-15.

Redfield M M. Epidemiology and pathophysiology of heart failure. *Curr Cardiol Rep* 2000; 2:179-80.

Feldman A M, Li Y Y, McTiernan C F. Matrix metalloproteinases in pathophysiology and treatment of heart failure. *Lancet* 2001; 357:654-5.

Francis G S, Wilson Tang W H. Pathophysiology of congestive heart failure. *Rev Cardiovasc Med* 2003; 4(suppl 2):S14-20.

McTiernan C F, Feldman A M. The role of tumor necrosis factor alpha in the pathophysiology of congestive heart failure. *Curr Cardiol Rep* 2000; 2:189-97.

Chen H H, Burnett J C. Natriuretic peptides in the pathophysiology of congestive heart failure. *Curr Cardiol Rep* 2000; 2: 198-205.

Perry L M. *Medicinal Plants of East and Southeast Asia.* Cambridge, Mass.: MIT Press (1980).

What is claimed is:

1. A method of therapeutic treatment for heart failure in a mammalian subject in need thereof suffering from or diagnosed with heart failure, wherein the heart failure results from myocardial infarction, comprising administering to the mammalian subject a composition comprising an effective amount of an organic extract of *Geum japonicum* and *Centella asiatica*, wherein the extract comprises:
   (i) one or more triterpenoids selected from the group consisting of: Asiatic acid, Niga-ichigoside F1, Kaji-ichigoside F1, Euscaphic acid, Asiaticoside, Tormentic acid, and Madecassic acid, and
   (ii) one or more polyphenols selected from the group consisting of: Gemin A, Casuarinin, Tellimagrandin II, Potentillin and ellagic acid.

2. The method of claim 1, wherein the composition comprises Asiatic acid, Niga-ichigoside F1, Kaji-ichigoside F1, Euscaphic acid, Asiaticoside, Tormentic acid, Madecassic acid, Gemin A, Casuarinin, Tellimagrandin II, Potentillin and ellagic acid.

3. The method of claim 1, wherein the subject is a human.

4. The method of claim 1, wherein the composition is administered orally, topically, systemically, intravenously, subcutaneously, intraperitoneally, or intramuscularly.

5. The method of claim 1, wherein the composition is administered in an amount of from 0.01 mg/kg/day to 1000 mg/kg/day.

6. The method of claim 1, wherein the effective amount of the composition is in the form of a pharmaceutical formulation comprising the composition and a suitable carrier or excipient therefore.

7. The method of claim 1, wherein the composition is administered in an amount ranging from about 0.001 mg to about 2000 mg of the extract per kilogram of subject body weight per day.

8. The method of claim 1, wherein the composition is administered orally.

9. The method of claim 1, wherein the composition is administered by subcutaneous injection, intramuscular injection, or intravenous infusion.

10. The method of claim 1, wherein the composition comprises a lower alkyl alcohol extract of *Geum japonicum* and *Centella asiatica*.

11. The method of claim 10, wherein the lower alkyl alcohol has 1-6 carbons atoms.

12. The method of claim 10, wherein the lower alkyl alcohol is ethanol.

* * * * *